June 2, 1942. R. L. BYRUM Plant Pat. 526
ROSE PLANT
Filed Dec. 2, 1941
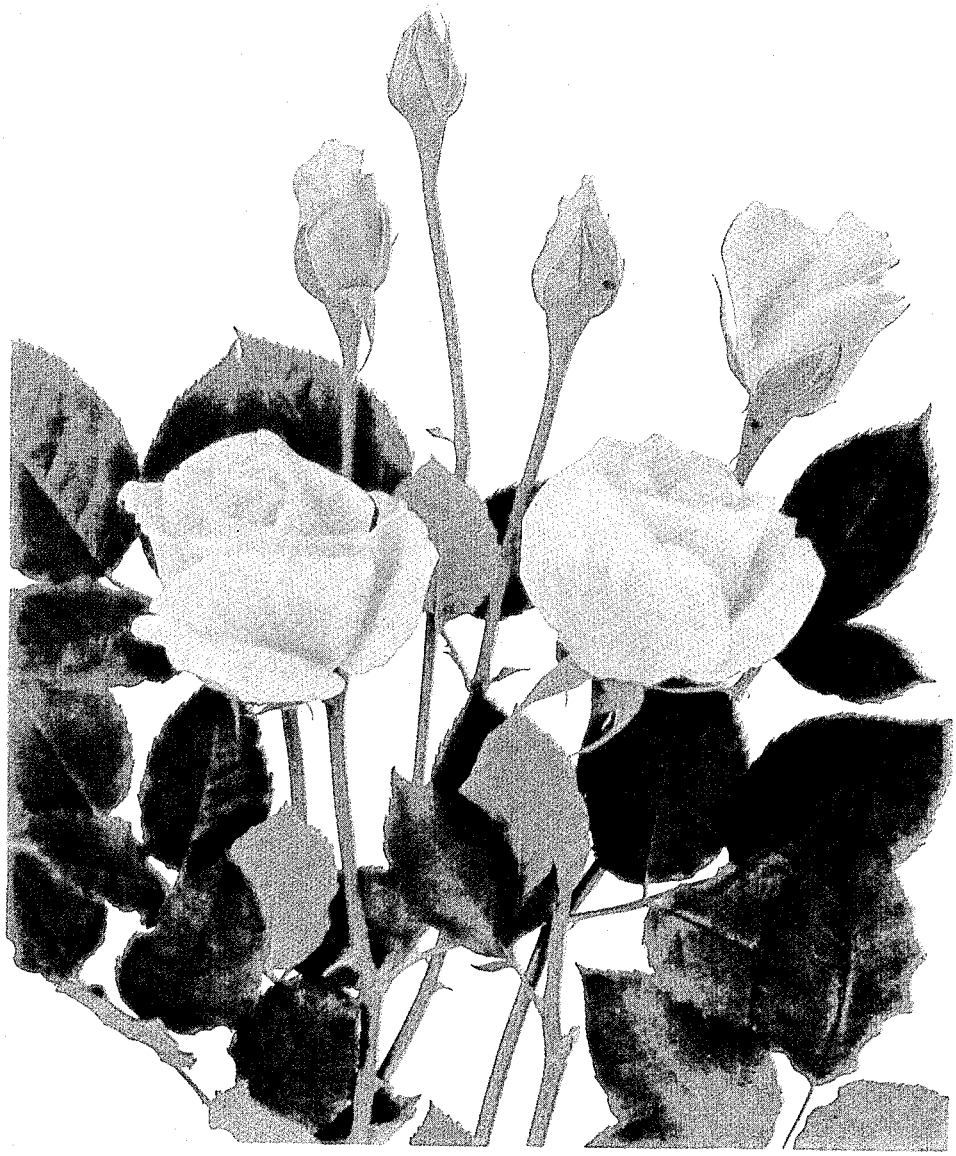
Inventor
R. L. Byrum
By Robb & Robb
attorneys Patented June 2, 1942

Plant Pat. 526

UNITED STATES PATENT OFFICE

526

ROSE PLANT

Roy L. Byrum, Richmond, Ind., assignor to Joseph H. Hill Company, Richmond, Ind., a corporation of Indiana Application December 2, 1941, Serial No. 421,358

1 Claim. (Cl. 47—61)

The present invention relates to a new and distinct variety of rose plant of the hybrid tea class, the result of crossing the two known varieties "Captain Glisson" (Plant Patent No. 155) and "Justine" (Plant Patent No. 154).

The object in view, in making this cross, was to obtain a variety of greater productivity in the class of greenhouse forcing roses than the pollen variety, and the rose produced not only possesses this characteristic, based on cutting records over a period of years in comparison with standard varieties, but combines with it an unusual color combination.

The new rose is unlike any other greenhouse forcing rose of which I am aware. It is slightly similar in color to "Justine" while in bud, and to "Captain Glisson" when open. Its color is the unusual combination of Light Ochraceous Buff and White, and while the canes of "Captain Glisson" are somewhat longer, the blooms have more petals than that variety, or even "Justine."

The new variety has been asexually reproduced and found to hold its distinguishing characteristics through succeeding propagations by cuttings, grafting, and budding.

The following is a detailed description of this new rose, color terminology being in accord with Ridgway's Color Standard and ordinary dictionary meaning:

Type: Bush; greenhouse; seedling; for cut flowers.

Class: Hybrid tea.

Parentage: Seedling.

*Seed parent.*—"Captain Glisson."

*Pollen parent.*—"Justine."

*Flower*

Locality where grown: Richmond, Indiana.

Flowers borne: Singly to stem; in irregular cluster; on strong, medium length stems.

Quantity of bloom: Abundant in greenhouse.

Continuity: Continuous.

Fragrance: Moderate; tea.

Bud:

*Peduncle.*—Short; heavy; erect; light green; smooth; numerous green hairs.

*Before calyx breaks.*—*Size*—medium, *Form*—short; pointed with a conspicuous neck; with foliaceous appendages on the surface of the bud; with slender foliaceous parts extending beyond the tip of the bud equal to one-fourth of its length.

*As calyx breaks.*—*Base*—Cream Color, Plate XVI. *Balance of bud*—Light Jasper Red, Plate XIII.

*As first petal opens.*—*Size*—medium large. *Form*—long; ovoid. *Color:* outside, base—Amber Yellow, Plate XVI, changing through Light Ochraceous Salmon, Plate XV, to almost pure White at tip of petal; inside, base—Amber Yellow, Plate XVI, changing through Warm-Buff, Plate XV, to White at tip of petal overlaid with slight shading of Pink—lighter than any Pink shown in Ridgway.

Opening—Opens up well.

Bloom:

*Size, when fully open.*—Medium large; four inches to five inches.

*Petalage.*—Very double; forty-five to fifty petals arranged regularly.

*Form.*—Open; full; becoming very open; petals remaining at first very tightly rolled outward; becoming later, at maturity, very loosely rolled outward.

Petals: Thick; inside, satiny; outside, shiny.

*Shape.*—Outside—Obovate with apex flat. Intermediate—obovate with apex flat. Inside—obovate; scalloped irregular, some with one notch and some with two.

This description of a newly opened flower was made from a rose grown in a greenhouse in the month of October, 1941, at Richmond, Indiana:

*Color.*—Outside petal: outside surface—base, Amber Yellow, Plate XVI, through Light Ochraceous Buff, Plate XV, on through Pale Vinaceous-Fawn, Plate XL, to almost White at tip of petal; inside surface—base, Wax Yellow, Plate XVI, penciled with Mustard Yellow, Plate XVI, almost White at tip of petal. Intermediate petal:—outside surface—base, Amber Yellow, Plate XVI, through Salmon Color, Plate XIV, to Pale Salmon Color, Plate XIV, at tip of petal; inside surface—base, Wax Yellow, Plate XVI, through Light Ochraceous Buff, Plate XV, penciled effect. Edge White. Inner petal: outside surface—base, Amber Yellow, Plate XVI, balance Flesh Color, Plate XIV; inside surface—base, Wax Yellow, Plate XVI, balance Light Ochraceous Buff, Plate XV.

This description was made from a rose that was open for three days in a greenhouse, in the month of October, 1941, at Richmond, Indiana:

*Color.*—Outside petal: outside surface—almost pure White, streaked with Amber Yellow, Plate XVI; inside surface—almost pure White, lightly penciled with Amber Yellow, Plate XVI. Inside petal: outside surface—Pale Salmon Color, Plate XIV; inside surface—White. *General color effect:* newly opened flower—Light Ochraceous Salmon, Plate XV; three days open—Pale Ochraceous Salmon, Plate XV.

*Behavior.*—Persist.

*Flower longevity.*—Cut roses grown in a greenhouse kept at living room temperatures four to five days in October.

*Productive Organs.*

Stamens: Many; arranged regularly about pistils.
Filaments: Medium long; white; most with anthers.
Anthers: Medium size; yellow; all open at once.
Pollen: Abundant; gold.
Pistils: Medium number.
Styles: Uneven; medium length; thin; very bunched.
Stigma: White.
Ovaries: Some protruding from calyx.
Sepals: Permanent; moderately short; spear-shaped.

*Color.*—Inside—Chromium Green, Plate XXXII, overlaid with fuzz. Outside—Chromium Green, Plate XXXII.

Hips: None as yet formed.
Seed: None as yet formed.

*Plant*

Foliage:

*Leaves.*—Compound of five leaflets; abundant; medium large; heavy.

*Leaflets.*—Ovoid with apex acute; base obtuse; margin simply serrate.

*Color.*—*Mature:* upper surface—moderately Dark Green; under surface—very Light Green. *Young:* upper surface—Light Green Bronze; under surface—Light Green.

*Rachis.*—Heavy; upper side, grooved, hairy; under side, smooth, prickly.

*Stipules.*—Very short; narrow; with short points turning out at an angle of less than 45°.

*Disease.*—Resistant to mildew and blackspot.

This characteristic was determined by growing this new variety next to a bench of a variety which has had blackspot throughout the season, and has also had mildew at various times. The new variety has remained clean the entire time, under identical growing and disease preventive conditions.

Growth:

*Habit.*—Bush; upright; much branched.

*Growth.*—Free; vigorous.

*Canes.*—Medium heavy.

*Main Stems.*—Green bronze. *Thorns*—several; medium long; hooked downward; with short, narrow base. *Prickles*—none. *Hairs*—none.

*Branches.*—Dull green. *Thorns*—several; medium length; hooked downward; with short, narrow base. *Prickles*—none. *Hips*—none.

*New Shoots.*—Dull green bronze. *Thorns*—several; medium long; hooked downward; short base. *Prickles*—none. *Hairs*—none.

I claim:

A new and distinct variety of rose plant, characterized as to novelty by its great productivity in the class of greenhouse forcing roses, the large size and number of petals of the bloom, and the unusual color combination of said bloom, substantially as shown and described.

ROY L. BYRUM.